(12) United States Patent
Stockstad

(10) Patent No.: US 6,353,363 B1
(45) Date of Patent: Mar. 5, 2002

(54) LOW VOLTAGE RAIL-TO-RAIL CMOS OUTPUT STAGE

(75) Inventor: Troy L. Stockstad, Chandler, AZ (US)

(73) Assignees: Gain Technology Corporation, Tucson, AZ (US); Seiko Instruments, Inc. (JP)

(*) Notice: Subject to any disclaimer, the term of this patent is extended or adjusted under 35 U.S.C. 154(b) by 0 days.

(21) Appl. No.: 09/515,961

(22) Filed: Feb. 29, 2000

(51) Int. Cl.[7] .............................................. H03F 3/18
(52) U.S. Cl. ...................................... 330/264; 330/268
(58) Field of Search .............................. 330/264, 267, 330/268

(56) References Cited

U.S. PATENT DOCUMENTS

| | | | |
|---|---|---|---|
| 4,087,759 A | * 5/1978 | Iwamatsu | .................... 330/262 |
| 4,335,355 A | * 6/1982 | Haque | ......................... 330/253 |
| 4,879,524 A | * 11/1989 | Bell | ............................. 330/288 |
| 5,006,815 A | 4/1991 | Klumperink et al. | |
| 5,293,136 A | 3/1994 | Ryan | |
| 5,376,899 A | 12/1994 | Pass | |
| 5,451,902 A | 9/1995 | Huang et al. | |
| 5,606,287 A | * 2/1997 | Kobayashi et al. | ......... 330/255 |
| 5,714,906 A | 2/1998 | Motamed et al. | |
| 5,889,433 A | * 3/1999 | Honma | ........................ 330/273 |
| 5,894,236 A | * 4/1999 | Mizoguchi et al. | ......... 327/108 |
| 6,060,940 A | * 5/2000 | Chiozzi | ....................... 327/437 |
| 6,121,839 A | * 9/2000 | Giacomini | ................... 330/264 |

* cited by examiner

*Primary Examiner*—Robert Pascal
*Assistant Examiner*—Henry Choe
(74) *Attorney, Agent, or Firm*—Oppenheimer Wolff & Donnelly

(57) ABSTRACT

An output stage suitable for low voltage operation and capable of providing an essentially symmetrical rail-to-rail output voltage is disclosed. The output stage includes a first field effect device having a first drain, a first gate, and a first source coupled to a power supply $V_{CC}$. The output stage further includes a second field effect device complimentary to the first field effect device, having a second drain, a second gate, and a second source coupled to a power supply having a nominal voltage of $V_{EE}$. Further, the second drain is coupled to the first drain. Also included in the output stage is an output sink network coupled to the second field effect device. The output sink network drives the second field effect device such that a product of a current in the first field effect device and a current in the second field effect device is essentially equal to a predetermined constant during operation of the output stage.

23 Claims, 5 Drawing Sheets

LOW VOLTAGE RAIL-TO-RAIL CMOS OUTPUT STAGE

CROSS REFERENCE TO RELATED APPLICATIONS

This application is related to co-pending U.S. patent application No. 09/516,008 entitled Low Voltage Rail-to-Rail CMOS Input Stage, filed on an even day herewith on behalf of Troy Stockstad, the disclosure of which is incorporated herein by reference.

BACKGROUND OF THE INVENTION

Operational amplifiers in current electronic devices are provided with an output stage for driving additional devices connected to the amplifier in a particular application. To be suitable for broad application, it is preferable to provide such output stages with various characteristics, such as a relatively large and symmetrical output swing, preferably rail-to-rail. It is also desirable to have the output able to both source and sink a substantial amount of current in order to drive loads having a significant capacitive component. In addition, the output should dissipate a relatively low quiescent power to minimize power consumption when not driving such loads. Obviously, other characteristics such as stability, manufacturability, etc. are also important considerations.

Most prior art output stages capable of operating at one volt are push-pull class A output stages. In this case either the pull-up or the pull-down device is a current source, and the other device is configured in a common-source configuration. This results in a high level of power dissipation to drive large output loads.

To minimize power dissipation in the output stage, class AB stages are often used. Such stages have relatively low quiescent power dissipation, yet are capable of driving large amounts of current.

In bipolar technologies, low voltage push-pull output stages generally rely on controlling base current drive to the output transistors. Since bipolar transistors are current driven devices, the output current of the device can be controlled if the base is driven with a controlled current source. Since collector current is exponentially dependent upon the base-mitter voltage, a large change in output current can be realized for small changes in the base-emitter voltage. Thus, in a bipolar design capable of operating at one volt, a circuit may be designed to control the base current drive of the device, yet still achieve a high output current. However, in a CMOS circuit such techniques are not effective since the amount of output current is strictly a function of the amount of voltage between the gate and the source of the device ($V_{GS}$).

CMOS push-pull output stages are generally designed such that one transistor is driven directly from the input of the output stage, and a complimentary transistor is driven by an output network. However, conventional CMOS output networks are problematic in that a conventional CMOS output network may or may not drive the complimentary transistor hard enough to create a symmetrical output. This problem is further increased at low voltages, such as at one volt.

Prior art FIG. 1 is a schematic diagram of a conventional CMOS output stage 100. The conventional output stage 100 includes P-channel transistor 102 and N-channel transistor 104 set in a push-pull configuration. In addition, output stage 100 includes P-channel transistor 106 and N-channel transistors 108, 110, and 112, as well as current source 114.

Conventional output stage 100 is an example of a IV CMOS push-pull output stage. Essentially, the drains of the P-channel transistor 102 and the N-channel transistor 104 are coupled together. In addition, the source of the P-channel transistor 102 is coupled to the positive power supply $V_{CC}$, while the source of the N-channel transistor 104 is coupled to the negative power supply $V_{EE}$. In this manner, the conventional output stage 100 achieves near rail-to-rail performance, until a load is placed at the output.

In order to provide negative drive capability, the conventional output stage 100 must be operated at a high quiescent current. Current source 114, along with the area ratios of NMOS transistors 108 and 104, set the maximum sink current capability of the output stage. The output sink current in NMOS 104 is controlled by replica PMOS transistor 106, which controls the bias to NMOS transistors 110 and 112. NMOS 110 then modulates the bias to output NMOS 104. The output drive capability of circuit 100 is not symmetrical, since the drain current in PMOS 102 is limited only by its $V_{GS}$, while the NMOS 104 can only deliver $I_{114}$ (($W/L_{104}$)/($W/L_{108}$)). This limits the type of applications that will function properly with output stage 100.

In view of the foregoing, what is needed is an output stage that provides near rail-to-rail performance, which does not require a high quiescent current to provide negative drive capability. Moreover, the output stage should be capable of operating from low supply voltages, such as slightly more than a single $V_{GS}$ voltage.

SUMMARY OF THE INVENTION

The present invention address this need by providing an output stage that provides essentially rail-to-rail performance, and operates from supply voltages down to slightly more than a single $V_{GS}$ voltage. In one embodiment, an output stage suitable for low voltage operation and capable of providing an essentially symmetrical rail-to-rail output voltage is disclosed. The output stage includes a first field effect device having a first drain, a first gate, and a first source coupled to a power supply $V_{CC}$. The output stage further includes a second field effect device complimentary to the first field effect device, having a second drain, a second gate, and a second source coupled to a power supply having a nominal voltage of $V_{EE}$. Further, the second drain is coupled to the first drain. Also included in the output stage is an output sink network coupled to the second field effect device. The output sink network drives the second field effect device such that a product of a current in the first field effect device and a current in the second field effect device is essentially equal to a predetermined constant during operation of the output stage.

In another embodiment, a method for providing an output signal from an output stage of a low voltage amplifier capable of providing a substantially rail-to-rail output voltage is disclosed. The method comprises providing an input signal to a first field effect device having a first drain, a first gate, and a first source coupled to a power supply $V_{CC}$. Next, a second complimentary field effect device is driven utilizing an output sink network such that the product of the current in the first field effect device and the current in the second field effect device is essentially equal to a predetermined constant during operation of the amplifier.

In yet another embodiment, an application specific integrated circuit (ASIC) having an output stage for a low voltage operational amplifier is disclosed. The ASIC includes a first field effect device having a first drain, a first gate, and a first source coupled to a power supply $V_{CC}$. The ASIC further includes a second field effect device complimentary to the first field effect device, having a second drain, a second gate, and a second source coupled to a power supply having a nominal voltage of $V_{EE}$. Further, the second drain is coupled to the first drain. Also included in the ASIC is an output sink network coupled to the second field effect device. The output sink network drives the second field effect device such that the product of the current in the first field effect device and the current in the second field effect device is essentially equal to a predetermined constant during operation of the output stage.

An operational amplifier output stage is disclosed in a further embodiment of the present invention. The operational amplifier output stage includes a push-pull output network that receives a first input signal and a second input signal, the first input signal being provided by an input signal $V_{IN}$. Also included in the operational amplifier output stage is an output sink network that provides the second input signal to the push-pull output network.

Finally, an operational amplifier suitable for operating on low input voltage and capable of providing a substantially symmetrical rail-to-rail output voltage is disclosed. The operational amplifier includes an input stage and an output stage coupled to the input stage. Further, the output stage includes an output sink network.

Advantageously, the present invention provides essentially rail-to-rail performance, and does not require a high quiescent current to provide negative drive capability. Furthermore, the output stage of the present invention is capable of operating from a low supply voltage of slightly more than a single $V_{GS}$ voltage.

BRIEF DESCRIPTION OF THE DRAWINGS

The invention, together with further advantages thereof, may best be understood by reference to the following description taken in conjunction with the accompanying drawings in which.

Prior Art

DETAILED DESCRIPTION OF THE INVENTION

An invention is disclosed for providing an output stage that achieves essentially symmetrical rail-to-rail performance, and can operate with a voltage supply of slightly more than a single $V_{GS}$ voltage. In the following description, numerous specific details are set forth in order to provide a thorough understanding of the present invention. It will be apparent, however, to those skilled in the art, that the present invention may be practiced without some or all of these specific details. In other instances, well known process steps have not been described in detail in order not to unnecessarily obscure the present invention.

Figure 1:
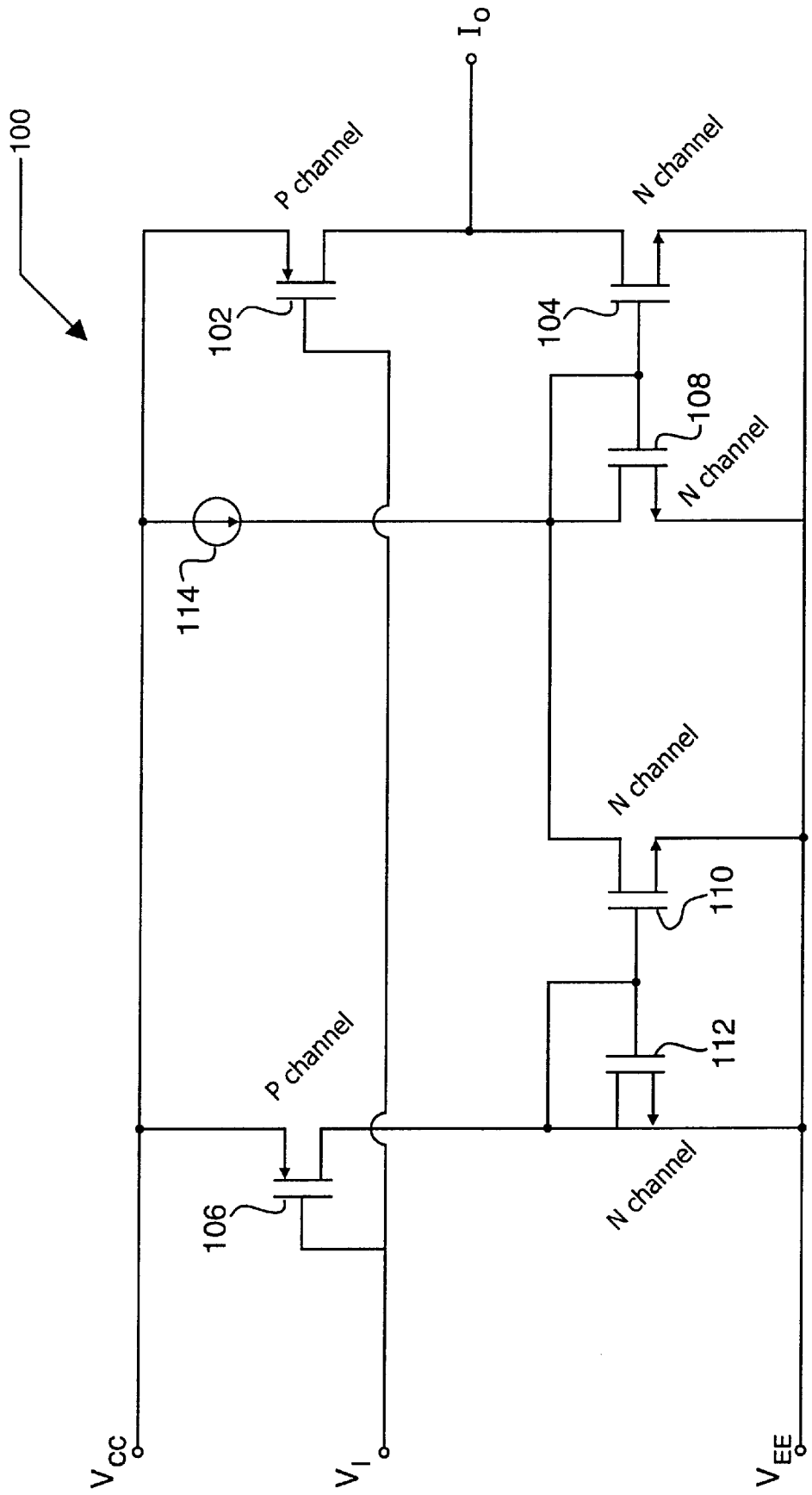
FIG. 1 is a schematic diagram of a conventional output stage.
Figure 2:
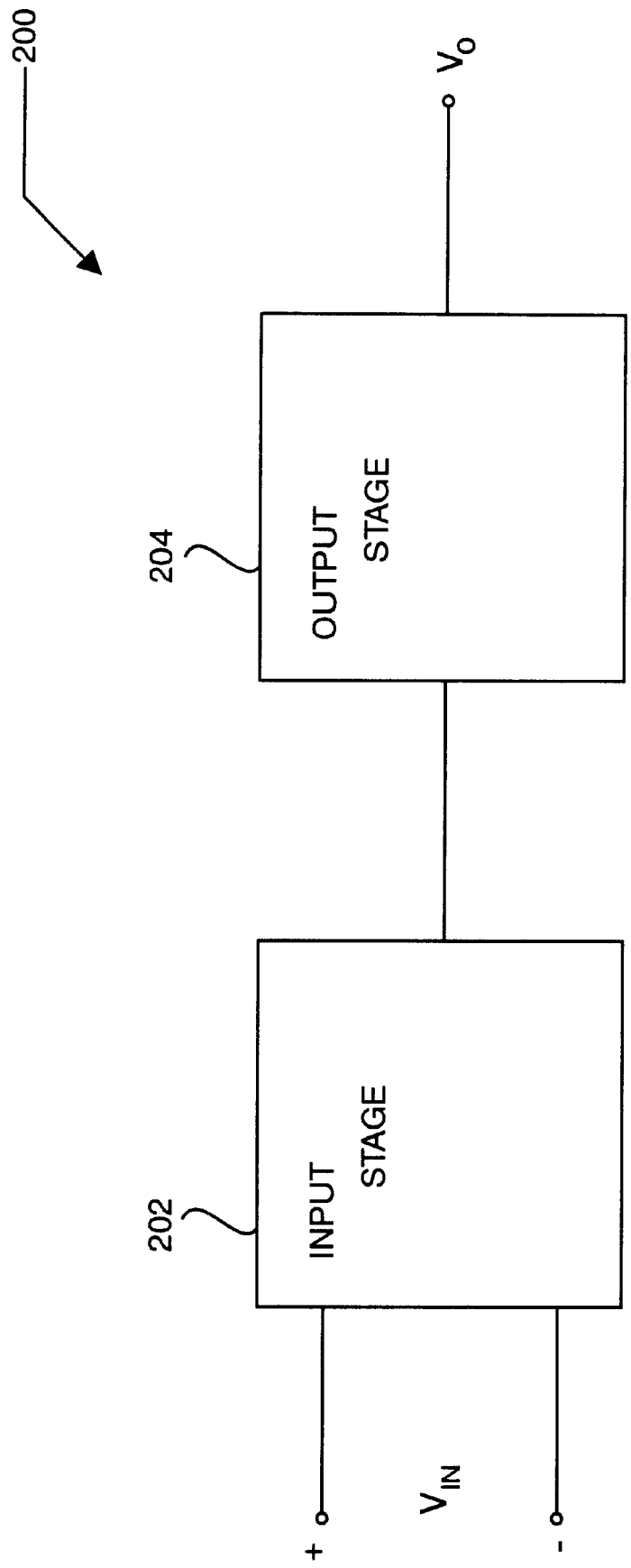
FIG. 2 is a block diagram showing an operational amplifier, in accordance with one embodiment of the present invention.

FIG. 1 was described in terms of the prior art. FIG. 2 is a block diagram showing an operational amplifier 200, in accordance with one embodiment of the present invention.

The operational amplifier 200 includes an input stage 202 and an output stage 204.

In operation, the input stage 202 receives a differential input signal $V_{IN}$. The input stage 202 then converts the differential input signal into a single output stage input signal, and then supplies the output stage input signal to the output stage 204. The output stage 204 receives the output stage input signal and converts it to an amplified output voltage $V_O$.

The output stage 204 provides essentially rail-to-rail performance, and is capable of operating with a voltage supply as low as essentially a single $V_{GS}$ voltage. As described in greater detail subsequently, the output stage 204 utilizes an output sink network to achieve this functionality.

Figure 3:
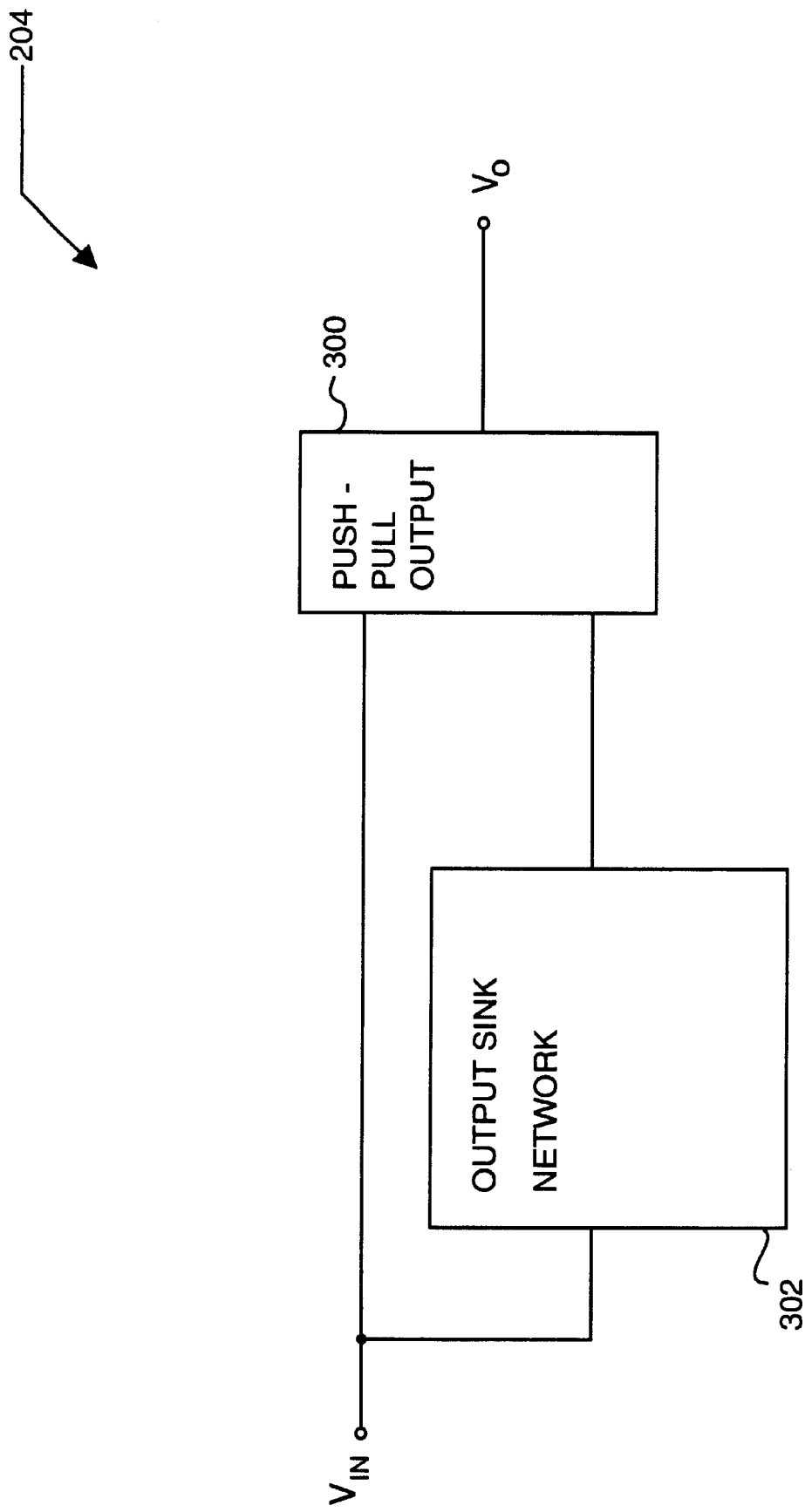
FIG. 3 is a block diagram of an output stage, in accordance with an embodiment of the present invention.

FIG. 3 is a block diagram of an output stage 204, in accordance with an embodiment of the present invention. The output stage 204 includes a push-pull output 300 and output sink network 302. In use, the push-pull output 300 receives two input signals. One signal is received from the source $V_{IN}$, the other signal is received from the output sink network 302.

As shown in FIG. 3, one side of the push-pull output 300 is driven directly by the source signal $V_{IN}$, while the other side is controlled by the output sink network 302. The result is an output stage 204 that provides a symmetrical rail-to-rail output when driven at one volt.

Figure 4:
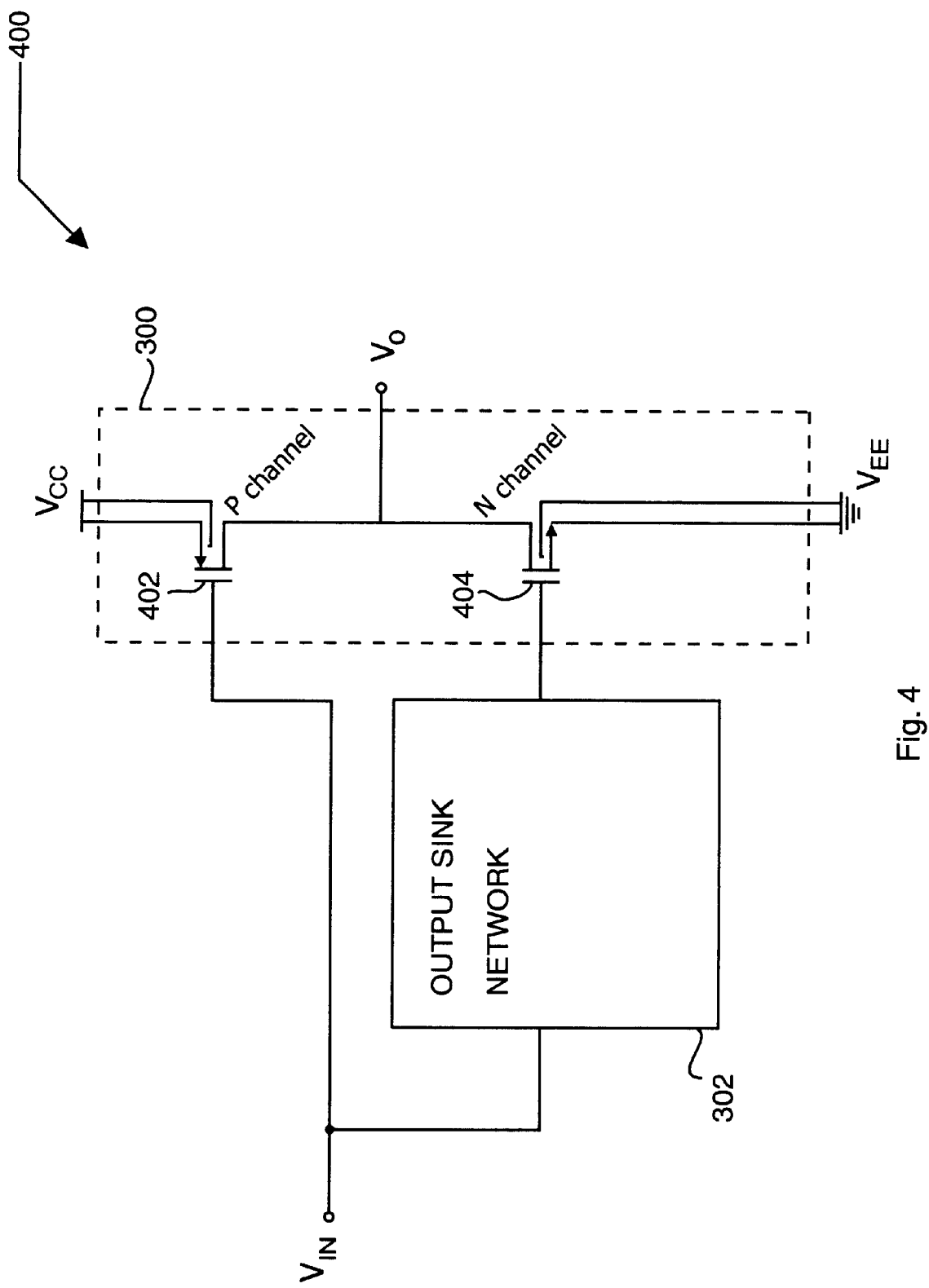
FIG. 4 is a schematic diagram of an output stage, in accordance with one aspect of the present invention.

Referring next to FIG. 4, an output stage 400 is shown, in accordance with one embodiment of the present invention. The output stage 400 includes an output sink network 302, and a push-pull output 300 having a P-channel transistor 402 and an N-channel transistor 404. The source of the P-channel transistor 402 is coupled to $V_{CC}$, while the source of the N-channel transistor 404 is coupled to $V_{EE}$. Finally, the drain of both the P-channel transistor 402 and the N-channel transistor 404 are coupled together.

In use, the P-channel transistor 402 is driven directly by the source voltage $V_{IN}$, while the N-channel transistor 404 is driven by the output sink network 302. To provide a push-pull output, the current in the P-channel transistor 402 and the N-channel transistor 404 are always equal to a constant when multiplied together.

Thus, the present invention drives the P-channel transistor 402 directly with the source voltage $V_{IN}$, and uses the output sink network to drive the N-channel transistor such that the product of the current in the P-channel transistor 402 and the N-channel transistor 404 is always equal to a predetermined constant. In other words, when the current in the P-channel transistor 402 is increased, the current in the N-channel transistor 404 is decreased, and vice-versa. It will be apparent to those skilled in the art that a similar approach is to connect voltage $V_{IN}$ to the gate of NMOS transistor 404, and have an output source network drive PMOS 402.

Figure 5:
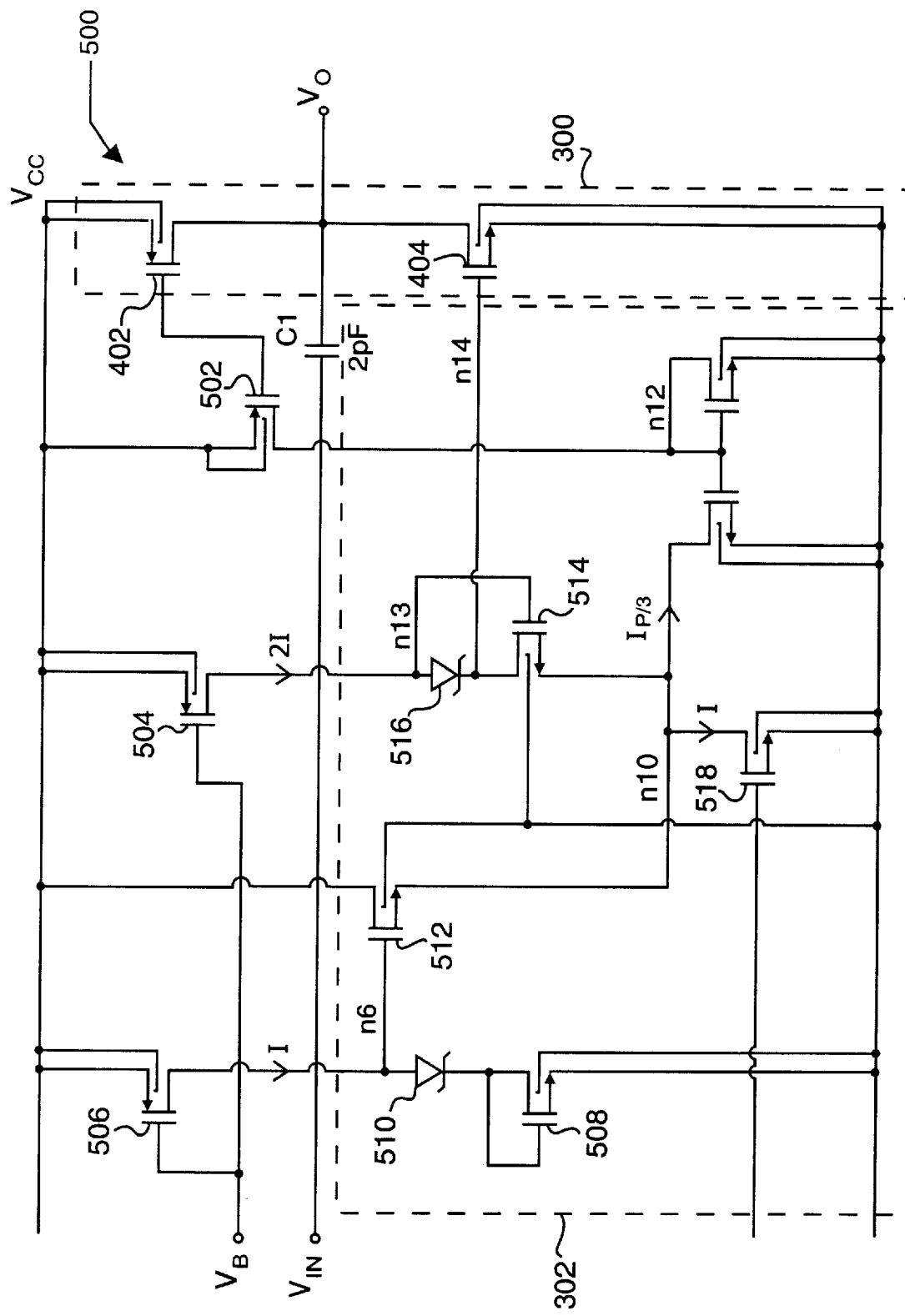
FIG. 5 is a schematic diagram of an output stage in accordance with another aspect of the present invention.

FIG. 5 is a schematic diagram of an output stage 500, in accordance with one aspect of the present invention. The output stage 500 includes a push-pull output 300 having P-channel transistor 402 and N-channel transistor 404, an output sink network 302, and P-channel transistors 502, 504, and 506.

The P-channel transistor 402 is configured in a common source configuration. P-channel transistor 502 is configured to replicate P-channel transistor 402 in order to track the current in transistor 402 at a predetermined ratio, such as 6:1. Thus, there is six times as much current in P-channel transistor 402 as there is in P-channel transistor 502. This current is then sent to the output sink network 302 to provide the above mentioned constant current product of transistors 402 and 404, as described in greater detail subsequently.

The output sink network 302 includes a loop of $V_{GS}$ voltages. Beginning on the left side of FIG. 5, N-channel transistor 508 is coupled in a diode connection providing one $V_{GS}$, and diode 510 provides a diode change to node n6. Both N-channel transistor 508 and diode 510 have a current I. Thus, node n6 is essentially a bias node having one $V_{GS}$ and one diode drop. Then from the gate of N-channel transistor 512 at node n6 to its source there is a one $V_{GS}$ drop. N-channel transistor 514 provides one $V_{GS}$ up from its source to its gate to node n13. Then back down one diode drop from diode 516. Finally, N-channel transistor 404 provides one $V_{GS}$ drop.

Thus, going through the loop of $V_{GS}$ voltages, there is the $V_{GS}$ for N-channel transistor 508, plus the diode drop of diode 510, minus a $V_{GS}$ of P-channel transistor 402, plus the $V_{GS}$ of N-channel transistor 514, minus the diode drop of diode 516, minus the $V_{GS}$ of N-channel transistor 404, all of which is equal to zero as set forth in the following equations:

$$(I_{P/3}-I)/(W/L_{512})=I_{DS12} \quad (1)$$

$$I_D=I_{D0}(W/L)\exp(V_{gs}/nV_T)\exp(-V_S/V_T)-\exp(-V_d/V_T) \quad (2)$$

$$nV_T \ln (I/(I_{D0}(W/L_{508}))+V_T \ln (I/I_S)-nV_T \ln ((I_{P/3}-I)/(I_{D0}(W/L_{512})))+nV_T \ln (2I/(I_{D0}(W/L_{514})))-V_T \ln (2I/2I_S)-nV_T \ln (I_N/(I_{D0}(W/L_{404})))=0 \quad (3)$$

$$2I^2/((W/L_{508})(W/L_{514}))=((I_{P/3}-I)(I_N))/((W/L_{512})(W/L_{404}))K_1=((I_P)(I_N))/(K_2) \rightarrow \text{push-pull action} \quad (4)$$

For quiescent point, $I_P=I_N=I_Q$

The above equations assume all MOSFETS operate in the sub threshold region. To calculate the quiescent current $I_Q$ the following equation can be used:

$$(2I^2)/((W/L_{508})(W/L_{514}))=((1/3)(I_Q^2)-(I_Q)(I))/((W/L_{512})(W/L_{404})) \rightarrow (1/3)(I_Q^2)-(I_Q)(I)-(2I^2)(((W/L_{512})(W/L_{404}))/((W/L_{508})(W/L_{514})))=0, \quad (5)$$

which can be solved using the quadratic equation.

Similar equations can be derived for the MOSFETS operating in saturation. Essentially, in saturation:

$$I_N+I_P=K, \quad (1)$$

wherein K is a constant value.

As can be seen in the above equations, diodes 510 and 516 cancel each other out. Their primary purpose is to create a voltage at the source of N-channel transistors 512 and 514 at node n10, which creates a current so the current sources can operate. In an alternate embodiment, diodes 510 and 516 may be replaced by resistors, which perform essentially the same function.

Referring to equation (3) above, two times $I^2$, which is set by N-channel transistors 506 and 504, divided by the size of N-channel transistors 508 and 514 is equal to $I_P$, which is the current in P-channel transistor 402, multiplied by $I_N$, which is the current in N-channel transistor 404, divided by three, which is derived from the ratio of transistors 402 and 502 and 520 and 522, times the size of transistors 402 and 404. Thus, a symmetrical rail-to-rail push-pull output is achieved.

In use, output stage 500 is connected to the output of the input stage, as shown in FIG. 2, and the P-channel devices are controlled directly. The output sink network 302 determines how to bias output P-channel transistor 402 such that a push-pull output is achieved.

In the present invention, there is no more than one $V_{GS}$ and two $V_{Dsat}$ from either rail. Thus, the present invention will operate at less than one volt.

In addition, unlike conventional output stages, the present invention is able to drive the gate voltage of N-channel transistor 404 to nearly $V_{CC}$. For example, if transistor 402 is turned off, so the gate voltage of transistor 402 is close to $V_{CC}$, the current in transistor 502 is reduced. But, transistor 504 is biased at 2I, while transistor 518 is biased at I. Thus, the voltage at the gate of transistor 404 will increase to within a saturation voltage of transistor 504 and the diode drop of diode 516. Thus, when the output is to be driven very hard, where the amplifier is open loop (i.e. the differential input voltage is large), the voltage at the gate of transistor 404 will increase dramatically, thus providing a very good output drive.

It should again be noted that although output stage 500 has been described with an output sink network to control NMOS 404, an alternative approach is to use an output source network similar to circuit 302 to drive PMOS 402, and drive NMOS 404 directly from input $V_{IN}$.

While the present invention has been described in terms of several preferred embodiments, there are many alterations, permutations, and equivalents which may fall within the scope of this invention. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

What is claimed is:

1. An output stage suitable for low voltage operation and capable of providing a substantially symmetrical rail-to-rail output voltage, the output stage comprising:

a first field effect device having a first source, first drain, and first gate, the first source being coupled to a power supply $V_{CC}$;

a second field effect device complementary to the first field effect device, wherein the second field effect device includes a second source, second drain, and second gate, and wherein the second source is coupled to a power supply having a nominal voltage supply of $V_{EE}$ and wherein the second drain is coupled to the first drain;

an output sink network coupled to the second gate, wherein the output sink network drives the second field effect device such that a product of a first current in the first field effect device and a second current in the second field effect device is essentially equal to a predetermined constant during operation of the out put stage; and said first and second field effect devices and said output sink network producing a symmetrical rail-to-rail output voltage of no more than on $V_{GS}$ and two $V_{DSAT}$ from either rail.

2. An output stage as recited in claim 1, wherein a sum of the first current and the second current is essentially equal to a predetermined constant during operation of the output stage.

3. An output stage as recited in claim 1, wherein the first field effect device is configured in a common source configuration.

4. An output stage as recited in claim 1, wherein the first field effect device is a P-channel metal oxide semiconductor field effect (PMOS) transistor.

5. An output stage as recited in claim 4, wherein the second field effect device is an N-channel metal oxide semiconductor field effect (NMOS) transistor.

6. An output stage as recited in claim 5, wherein the output sink network utilizes a current mirror to track the current in the first field effect device.

7. An output stage as recited in claim 6, wherein the current mirror tracks the current in the first field effect device at a predetermined ratio of the current in the first field effect device.

8. An output stage as recited in claim 1, wherein the first field effect device is an N-channel metal oxide semiconductor field effect (NMOS) transistor.

9. An output stage as recited in claim 8, wherein the second field effect device is a P-channel metal oxide semiconductor field effect (PMOS) transistor.

10. A method for providing an output signal from an output stage of a low voltage operation amplifier capable of providing a substantially rail-to-rail output voltage, the method comprising the operations of:

provJiding an input signal to a first field effect device having a first source, first drain, and first gate, the first source being coupled to a power supply $V_{CC}$;

driving a second complementary field effect device utilizing an output sink network such that a product of a first current in the first field effect device and a second current in the second field effect device is essentially equal to a predetermined constant during operation of the amplifier; and producing a symmetrical rail-to-rail output voltage, the rail-to-rail output voltage being no more than one $V_{GS}$ and two $V_{DSAT}$ from either rail.

11. A method as recited in claim 10, wherein a sum of the first current and the second current is essentially equal to a predetermined constant during operation of the amplifier.

12. A method as recited in claim 10, wherein the first field effect device is configured in a common source configuration.

13. A method as recited in claim 12, wherein the first field effect device is a P-channel metal oxide semiconductor field effect (PMOS) transistor.

14. A method as recited in claim 13, wherein the second field effect device is an N-channel metal oxide semiconductor field effect (NMOS) transistor.

15. A method as recited in claim 14, further comprising the operation of tracking the current in the first field effect device utilizing a current mirror.

16. A method as recited in claim 15, wherein the current mirror tracks the current in the first field effect device at a predetermined ratio.

17. An application specific integrated circuit (ASIC) having an output stage for a low voltage operational amplifier, the ASIC comprising:

a first field effect device having a first source, first drain, and first gate, the first source being coupled to a power supply $V_{CC}$;

a second field effect device complementary to the first field effect device, wherein the second field effect device includes a second source, second drain, and second gate, and wherein the second source is coupled to a power supply having a nominal voltage supply of $V_{EE}$ and wherein the second drain is coupled to the first drain;

an output sink network coupled to the second gate, wherein the output sink network drives the second field effect device such that a product of a first current in the first field effect device and a second current in the second field effect device is essentially equal to a predetermined constant during operation of the output stage; and said first and second field effect devices and said output sink network producing a symmetrical rail-to-rail output voltage of no more than one $V_{GS}$ and two $V_{DSAT}$ from either rail.

18. An ASIC as recited in claim 17, wherein the first field effect device is configured in a common source configuration.

19. An ASIC as recited in claim 17, wherein the first field effect device is a P-channel metal oxide semiconductor field effect (PMOS) transistor.

20. An ASIC as recited in claim 19, wherein the second field effect device is an N-channel metal oxide semiconductor field effect (NMOS) transistor.

21. An ASIC as recited in claim 20, wherein the output sink network utilizes a current mirror to track the current in the first field effect device.

22. An ASIC as recited in claim 21, wherein the current mirror tracks the current in the first field effect device at a predetermined ratio.

23. An ASIC as recited in claim 22, wherein the predetermined ratio is about 6:1.

\* \* \* \* \*